(12) United States Patent
Balaban et al.

(10) Patent No.: US 10,889,847 B2
(45) Date of Patent: Jan. 12, 2021

(54) KIT AND DISCS FOR USE IN DISC DIFFUSION ANTIBIOTIC SENSITIVITY TESTING

(71) Applicant: YISSUM RESEARCH DEVELOPMENT COMPANY OF THE HEBREW UNIVERSITY OF JERUSALEM LTD., Jerusalem (IL)

(72) Inventors: Natalie Balaban, Mevasseret Zion (IL); Orit Gefen, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 135 days.

(21) Appl. No.: 15/768,610

(22) PCT Filed: Oct. 18, 2016

(86) PCT No.: PCT/IL2016/051126
§ 371 (c)(1),
(2) Date: Apr. 16, 2018

(87) PCT Pub. No.: WO2017/068576
PCT Pub. Date: Apr. 27, 2017

(65) Prior Publication Data
US 2018/0305732 A1    Oct. 25, 2018

Related U.S. Application Data

(60) Provisional application No. 62/244,809, filed on Oct. 22, 2015.

(51) Int. Cl.
*C12Q 1/18* (2006.01)
*C12Q 1/24* (2006.01)

(52) U.S. Cl.
CPC ............. *C12Q 1/18* (2013.01); *C12Q 1/24* (2013.01)

(58) Field of Classification Search
None
See application file for complete search history.

(56) References Cited

PUBLICATIONS

Driscoll, Amanda J; et al; "Disk Diffusion Bioassays for the Detection of Antibiotic Activity in Body Fluids: Applications for the Pneumonia Etiology Research for Child Health Project" Clinical Infection Diseases, 54, S2, S159-S164, 2012 (Year: 2012).*
Coyle M. (editor), "Manual of antimicrobial susceptibility testing". American society for microbiology, Jan. 1, 2005, pp. 1-236.
Kosher S., "Growth factors for Microorganisms",Annual review of microbiology, Oct. 1, 1948, vol. 1, No. 1, pp. 121-142 (22 pages).
Brauner A. et al., "Distinguishing between resistance, tolerance and persistence to antibiotic treatment", Nature reviews microbiology, May 1, 2016, vol. 14, pp. 320-330 (12 pages).
International Search Report for PCT/IL2016/051126, dated Jan. 26, 2017 (4 pages).
Written Opinion of the International Searching Authority for PCT/IL2016/051126, dated Jan. 26, 2017 (9 pages).

* cited by examiner

*Primary Examiner* — David W Berke-Schlessel
(74) *Attorney, Agent, or Firm* — Roach Brown McCarthy & Gruber, P.C.; Kevin D. McCarthy

(57) ABSTRACT

The present invention provides methods and kits for performing microbial sensitivity tests. Specifically, the invention relates to methods for identifying the susceptibility, tolerance or resistance of a microorganism to one or more antimicrobial agents, and the level of tolerance. The method comprises exposing the microorganism grown on a plate surface to one or more antimicrobial agents and to at least one growth promoting agent.

1 Claim, 15 Drawing Sheets

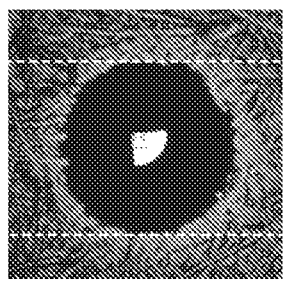 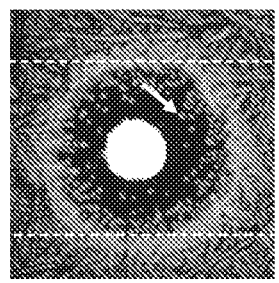 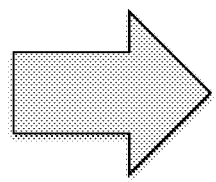 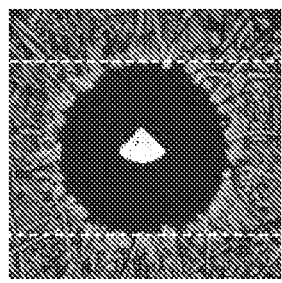
FIG. 7A  FIG. 7B  FIG. 7C

Imipenem
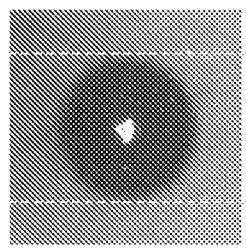 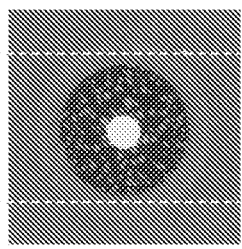 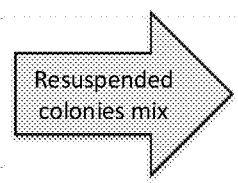 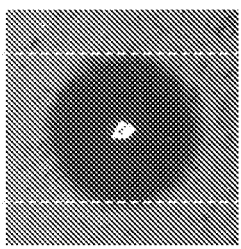
FIG. 14A    FIG. 14B    FIG. 14C Ampicillin
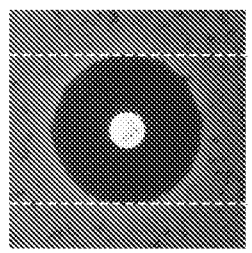 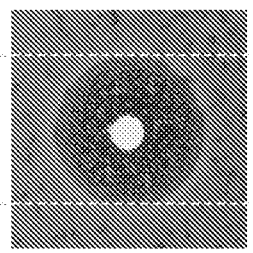 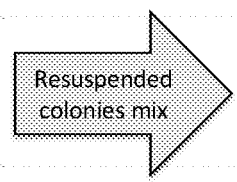 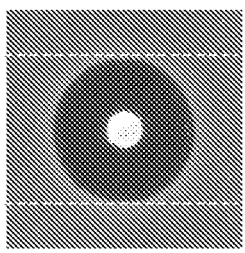
FIG. 15A  FIG. 15B  FIG. 15C

KIT AND DISCS FOR USE IN DISC DIFFUSION ANTIBIOTIC SENSITIVITY TESTING

FIELD OF THE INVENTION

The present invention is in the field of microbiology. The invention relates to a method for performing microbial sensitivity tests.

BACKGROUND OF THE INVENTION

The main reason for the failure of antibiotic treatments is bacterial resistance. In general, studies of bacterial antibiotic resistance have focused on the inherited genetic mutations that underlie resistance. The isolation and genetic characterizations of resistant mutants have uncovered many molecular mechanisms of resistance, including alterations in drug target and direct inactivation of the drug, to name a few.

However, it was already clear in 1944 that antibiotic treatments may fail even without the appearance of resistance. Bacteria were able to survive extensive antibiotic treatments without having acquired a resistance mutation.

The terms "tolerance" and "persistence" were coined to distinguish these survival modes from "resistance". Discrimination between the different strategies for survival is crucial for identifying mechanisms related to survival and for devising effective treatment regimens. Clearly, attempts to apply the same treatment to survival strategies that, despite superficial similarities, differ in their basic mode of action, will be ineffective.

In contrast to resistance, which enables bacteria to grow in a concentration of a drug that would otherwise prevent growth, tolerance is only a transient ability of bacteria to survive under otherwise bactericidal treatments. The term "persistence" is commonly used when only a small subpopulation of bacteria within a susceptible population survives the antibiotic treatment.

Most studies of antibiotic treatment failure start with the isolation of bacterial strains with higher survival under an antibiotic treatment, but the knowledge of the underlying molecular mechanism responsible for survival may be attained, if at all, only after many additional studies. Nevertheless, it is important to determine the class of survival strategies at work by in vitro characterizations, even without this knowledge. The current practice in the clinic is to characterize resistance only, as described below, but tolerance is overlooked.

The "disk diffusion antibiotic sensitivity testing", also termed "Kirby-Bauer antibiotic testing", is a standardized technique (since 1959) clinically used to test the effects of different antibiotics on bacteria, and determine whether they are susceptible or resistant to each antibiotic. In this assay, one or more disks impregnated with fixed concentrations of antibiotics are placed on a gel plate (e.g. an agar plate) where bacteria have been previously plated. After incubation (e.g. 18-24 hours at 37° C.), the diameter of zones of inhibition around the disks (if present) determine the sensitivity or resistance of the microorganism to the particular antimicrobial agent impregnated in each disk. During incubation, a gradient of antibiotic concentrations is formed in the agar away from the disk, which prevents the growth of susceptible microorganisms in the area where the concentration of the antibiotics is higher than the Minimum Inhibitory Concentration (MIC). The results are read after overnight incubation.

Killing tolerant bacterial culture requires longer antibiotic treatment, but not higher dose of antibiotics, compared to a sensitive bacteria culture. The "disk diffusion" method is designed to identify susceptible and resistant bacteria by creating a gradient of antibiotic concentration that enables the evaluation of the concentration at which a bacterial strain stops growing, namely the resistance level. However, a clear difference between tolerant and susceptible bacteria is not seen in that assay, because tolerant bacteria that survive the antibiotic treatment are deprived of nutrients by the adjacent growing bacteria, and therefore are not able to develop and form visible colonies. Accordingly, tolerance strains are not detected using the standard disk diffusion assay.

Late-growing bacteria, leading to tolerance or persistence, may survive an antibiotic treatment and might lead to treatment failure. The level of tolerance of an isolate to a particular drug is, however, not taken into account when choosing antibiotics. At present, a major limitation of addressing the phenomenon of tolerance in the clinic is the absence of a simple detection technique for tolerant strains.

It is therefore an object of the present invention to provide a method for determining whether a microorganism, such as bacterium, is susceptible, tolerant or persistent to a tested antimicrobial agent.

It is another object of the invention to provide a method for detecting different levels of antibiotic tolerance in clinical bacterial isolates.

It is still another object of the invention to provide a clinical tool for identifying one or more antibiotic that effectively eliminates tolerant bacteria.

SUMMARY OF THE INVENTION

According to a first aspect, the invention relates to a method for identifying the susceptibility, tolerance or resistance of a microorganism to one or more antimicrobial agent, comprising the following steps:
  a. inoculating a microorganism on a growth plate;
  b. exposing the surface of the plate to one or more antimicrobial agents;
  c. optionally incubating the plate for a first period of time;
  d. exposing the surface of the plate to least one growth promoting agent;
  e. incubating the plate for a second period of time;
  f. observing the growth pattern of said microorganism on said plate.

The susceptibility, tolerance or resistance of said microorganism to said antimicrobial agent is determined according to the presence and growth pattern within the inhibition zone.

The microorganism is selected from a bacterium, a fungi, a yeast and a parasite. According to a specific embodiment, the microorganism is a bacterium. The antimicrobial agent is selected from an antibiotic, antifungal, biocide, germicide, antiseptic, disinfectant and preservative. According to a specific embodiment, the antimicrobial agent is an antibiotic.

The at least one growth promoting agent according to the invention is a nutrient or a growth factor, or any combinations thereof. According to one specific embodiment, the nutrient is selected from a sugar, an amino acid, a lipid, a fatty acid, a mineral, and a vitamin. More specifically, the sugar is glucose. According to another specific embodiment, the growth factor is a pH changing chemical selected from an acid, a base and a buffering agent. Furthermore, the growth factor is selected from an antibiotic degrading agent, an antibiotic deactivating agent, an antibiotic inhibitor, an activator of intrinsic resistance factors in the microorganism. According to a further specific embodiment, said at least one growth promoting agent according to the invention comprises any combination of two or more nutrients or a growth factors as specified above.

In some embodiments of the invention, the antimicrobial agent is applied to the microorganism growth plate by a disk containing a single concentration of the agent. Alternatively, the antimicrobial agent is applied by several disks, each containing a different concentration of the agent. Still alternatively, the antimicrobial agent is applied by a strip containing several concentrations of the same agent.

The growth promoting agent is applied by a disk containing a single concentration of the agent. Alternatively, the growth promoting agent is applied by dripping a solution of the agent onto the plate.

It should be noted that in some embodiments of the method of the invention, the disk or strip comprising the antimicrobial agent is removed after a period of time and replaced by a disk or a solution comprising at least one growth promoting agent. In one embodiment, the growth promoting agent is applied at the center of the disk or strip containing the antimicrobial agent. The first period of time and said second period of time according to the invention are each between about 6 and about 30 hours. More specifically, the first period of time and the second period of time are each about 18 hours.

In other embodiments of the method of the invention, the antimicrobial agent and the growth promoting agent are applied at the same time, simultaneously. In such cases, the step designated as the first period of time incubation is not performed, and only the incubation designated as the second period of time is carried out. When the antimicrobial agent and the growth promoting agent are applied at the same time, the promoting agent is designed to diffuse in a slower rate than the antimicrobial agent. According to one embodiment, the slower diffusion rate is achieved by applying the growth promoting agent after a first period of time incubation by placing a separate disk or by dripping a solution onto the plate.

In other embodiments of the invention, the antimicrobial agent and the growth promoting agent are present in a single disk, such as in two regions or layers, optionally separated by a degradable barrier. In further embodiments, the single disk composed of different carrier materials, wherein the material holding the antimicrobial agent allows faster diffusion therefrom compared to the material holding the growth promoting agent. It should be noted that in cases of a single disk, the growth promoting agent is released from the disk in a slower rate, or has a significantly smaller diffusion constant, compared to the antimicrobial agent. The slower release rate is due to the larger size of the growth promoting agent, or growth promoting agent particles, compared to the size of the antimicrobial agent or the antimicrobial agent particles. Alternatively, the slower release rate is due to the presence of a larger amount of the growth promoting agent compared to the antimicrobial agent in the disk. Still alternatively, the slower release rate is due to the initial spatial location in the disk of the growth promoting agent and the antimicrobial agent. In some embodiments, the growth promoting agent is present in the disk in aggregates or crystals. In yet other embodiments, the growth promoting agent is present in the disk in degradable nanoparticle, nanocapsules, or liposomes.

According to another aspect, the invention relates to a kit comprising:
a. several disks containing the same antimicrobial agent at different concentrations;
b. at least one growth promoting agent; and
c. instructions for use.

In one embodiment of the kit of the invention, the growth promoting agent is provided on a disk. In another embodiment, the growth promoting agent is provided as a solution in a vial. The kit may optionally further comprise one or more microorganism growth plates, each comprising at least one growth promoting agent.

According to a further aspect, the invention relates to a method for identifying the level of tolerance or and persistence of a microorganism to one or more antimicrobial agent, comprising:
a. inoculating a microorganism on a growth plate;
b. exposing the surface of the plate to an antimicrobial agent;
c. optionally incubating the plate for a first period of time;
d. exposing the surface of the plate to several concentrations of a growth promoting agent;
e. incubating the plate for a second period of time;
f. observing the growth pattern of said microorganism on said plate.

The level of tolerance or and persistence of the microorganism to the antimicrobial agent is determined according to the presence and growth pattern within the inhibition zone.

All the above and other characteristics and advantages of the invention will be further understood through the following illustrative and non-limitative description of embodiments thereof, with reference to the appended Figures.

BRIEF DESCRIPTION OF THE DRAWINGS

FIG. 1A is a schematic plot of the fraction of surviving bacteria in batch culture for a resistant strain (solid line), tolerant strain (dashed line) and susceptible strain (dotted line).

FIG. 1B shows the results obtained by standard Disk diffusion assay of a resistant bacterial strain. No inhibition zone is visible.

FIG. 1C shows the results obtained by standard Disk diffusion assay of a tolerant bacterial strain (tbl3a). A growth inhibition zone around the antibiotics disk is visible.

FIG. 1D shows the results obtained by standard Disk diffusion assay for a susceptible strain (KLY) having the same MIC as the tolerant strain shown in FIG. 1C. A growth inhibition zone around the antibiotics disk is visible.

Abbreviations: SF (survival fraction); T (time); h (hours).

Figure 2A:
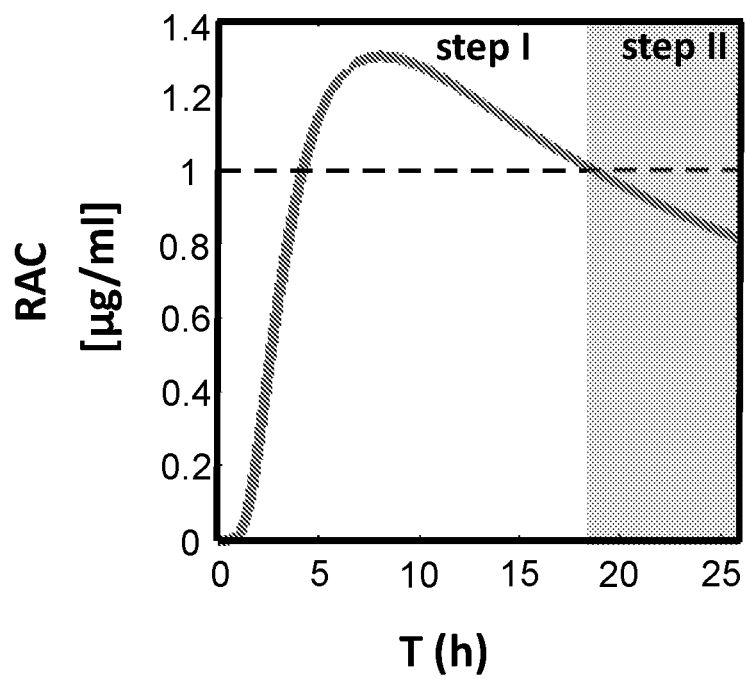
Figure 2B:
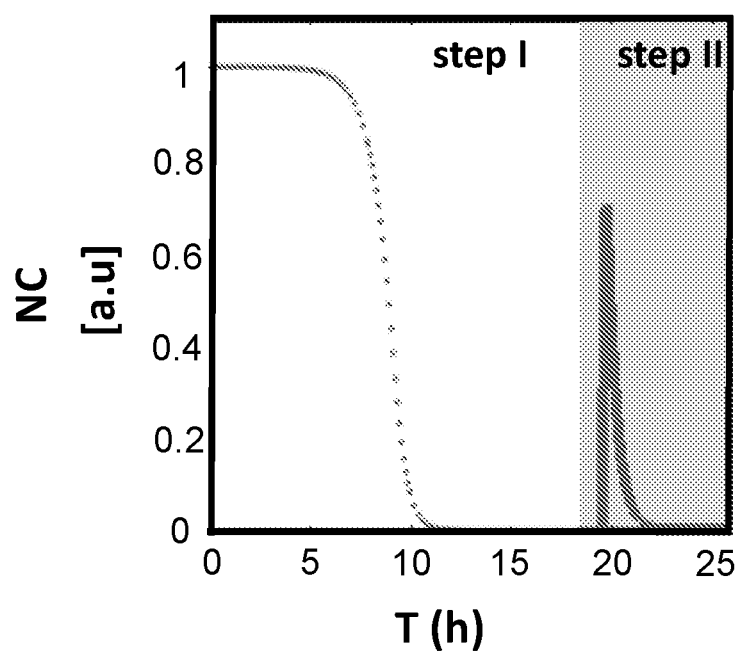

FIG. 2A-2B show schematic plots.

FIG. 2A is a schematic antibiotic concentration profile over time at a point in the inhibition zone (0.8 cm from the center of the antibiotic disk), assuming a point-source diffusion profile.

FIG. 2B is a schematic nutrient concentration profile over time at the same point as in A, assuming a point-source diffusion profile.

Abbreviations: AC (antibiotic concentration); NC (nutrient concentration); a.u. (arbitrary units); T (time); h (hours).

Figure 3A:
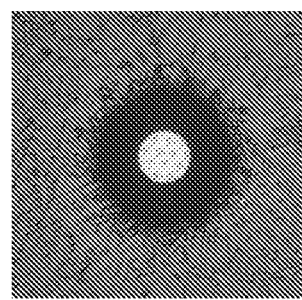
Figure 3B:
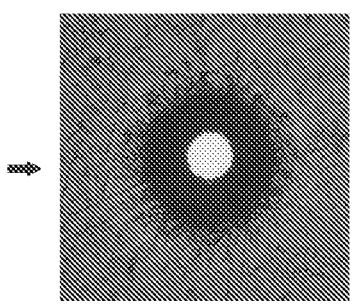
Figure 3C:
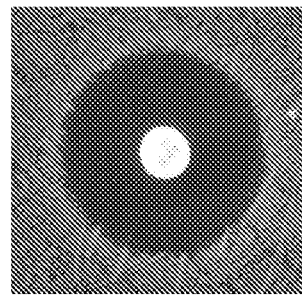
Figure 3D:
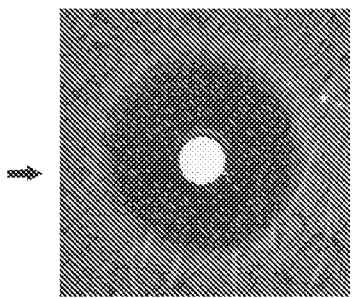

FIG. 3A-3D show the growth of susceptible and tolerant bacterial strains after each step of the Tolerance Diffusion test (TDtest). The growth of a susceptible strain is inhibited around the antibiotic disk after step I (FIG. 3A), and no late growth is evident after glucose addition according to step II (FIG. 3B). The growth of a tolerant strain is inhibited around the antibiotic disk after step I (FIG. 3C). After the addition of glucose, colonies are visible inside the growth inhibition zone, indicating slow or late growing bacteria of this strain (FIG. 3D).

Figure 4A:
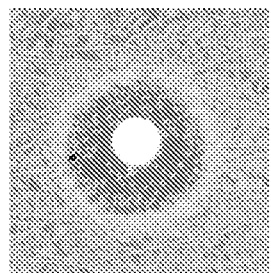
Figure 4B:
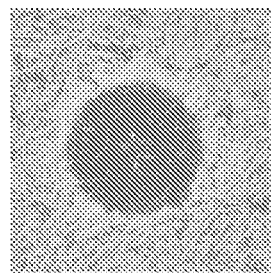
Figure 4C:
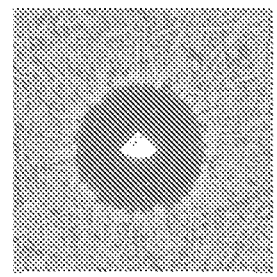

FIG. 4A-4C shows the growth of the strain W574 after 32 hours experiments in response to different conditions.

FIG. 4A shows the bacterial growth after the end of the TDtest (steps I and II).

FIG. 4B shows the bacterial growth after antibiotic treatment, removal of antibiotic disk, and incubation without the addition of a nutrient disk.

FIG. 4C shows the bacterial growth after antibiotic treatment, as in FIG. 4B, but without the removal of the antibiotic disk.

Figure 5A:
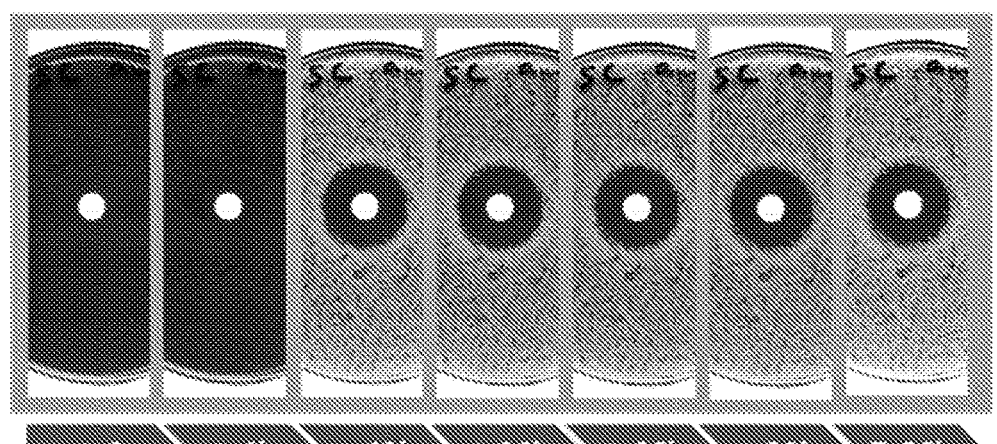
Figure 5B:
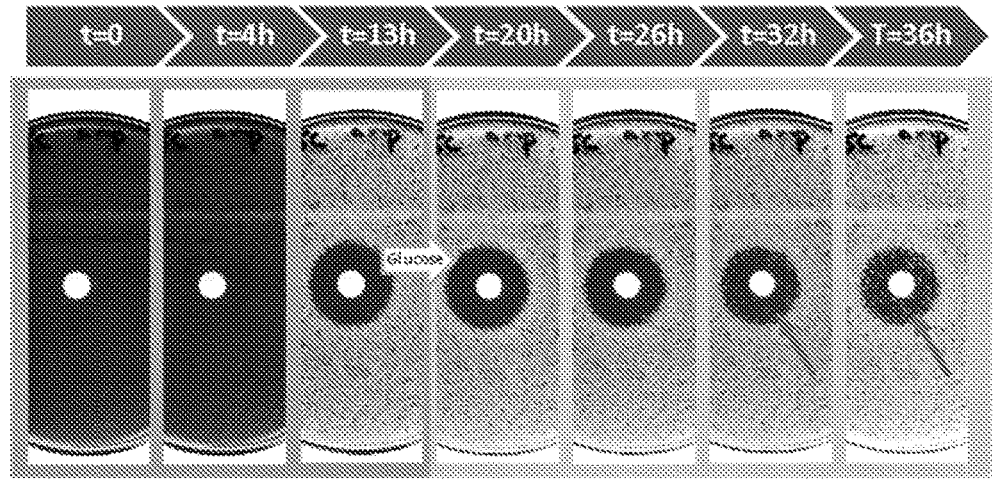

FIG. 5A-5B show the growth over time (0, 4, 13, 20, 26, 32 and 36 hours) of the E. cloacae clinical strain B340 in response to ampicillin by the standard disk diffusion assay (FIG. 5A) and the TDtest (FIG. 5B).

Abbreviations: T (time); h (hours).

FIG. 6A-6E show bacterial colonies inside the growth inhibition zone after the second step of the TDtest.

Figure 6A:
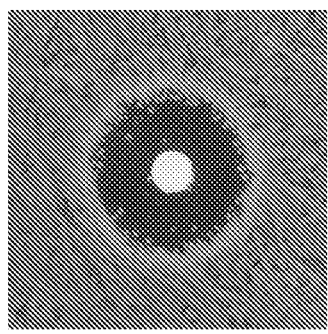

FIG. 6A shows the growth of a low-tolerance WT strain.

Figure 6B:
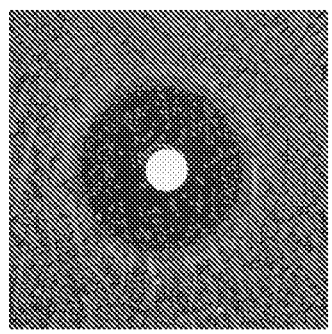

FIG. 6B shows the growth of a medium-tolerance vapB mutant strain (tbl3a).

Figure 6C:
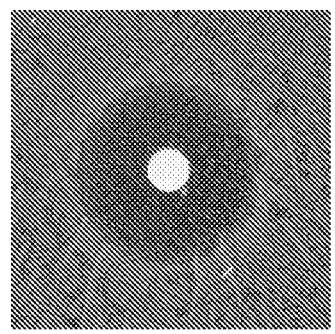

FIG. 6C shows the growth of a high-tolerance metG mutant strain (tbl5a).

Figure 6D:
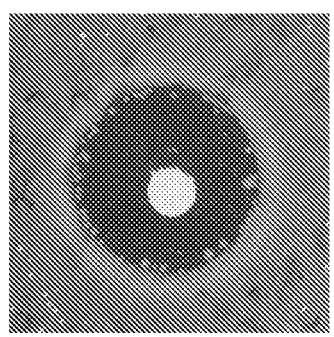

FIG. 6D shows the growth of a low-persistence WT strain (MGY).

Figure 6E:
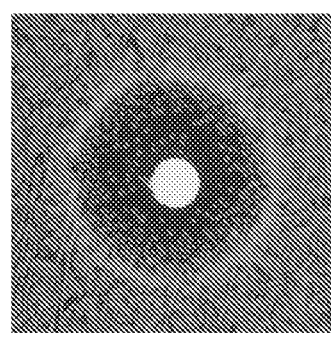

FIG. 6E shows the growth of a hipA7 high-persistence mutant (MGHY).

FIG. 7A-7C show bacterial colonies inside the growth inhibition zone after step I (FIG. 7A), step II (FIG. 7B) of the TDtest and the standard disk diffusion assay of a re-suspended colony obtained in step II.

FIG. 7A shows the growth in the inhibition zone after the first step of the TDtest (exposure to antibiotics only). The dashed lines mark the diameter of the inhibition zone.

FIG. 7B shows the growth in the inhibition zone after the second step of the TDtest (replacement of the antibiotic disk with a glucose-containing disk). Appearance of colonies inside the inhibition zone occurs after a few hours and indicates tolerant/persistent bacteria. The white arrow points to a colony that grew inside the inhibition zone.

FIG. 7C shows the growth in the inhibition zone of a colony that was picked and retested from the inhibition zone after the TDtest (panel B, white arrow), and re-suspended and examined according to the standard diffusion assay using the same antibiotic as in FIG. 7A. The dashed lines mark the diameter of the inhibition zone.

FIG. 8A-8E show results for E. coli strains U453 and W574 treated with ertapenem.

Figure 8A:
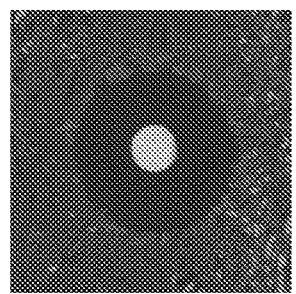

FIG. 8A shows U453 growth after step I of the TDtest, namely standard exposure to ertapenem disk (0.25 microgram).

Figure 8B:
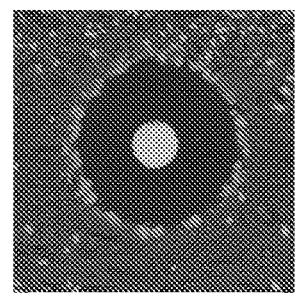

FIG. 8B shows U453 growth at the end of step II of the TDtest.

Figure 8C:
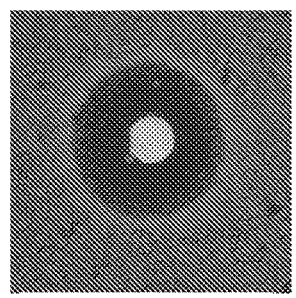

FIG. 8C shows W574 growth after step I of the TDtest, namely standard exposure to ertapenem disk (0.25 microgram).

Figure 8D:
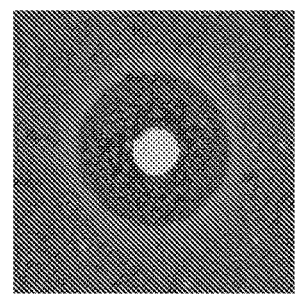

FIG. 8D shows W574 growth at the end of step II of the TDtest.

Figure 8E:
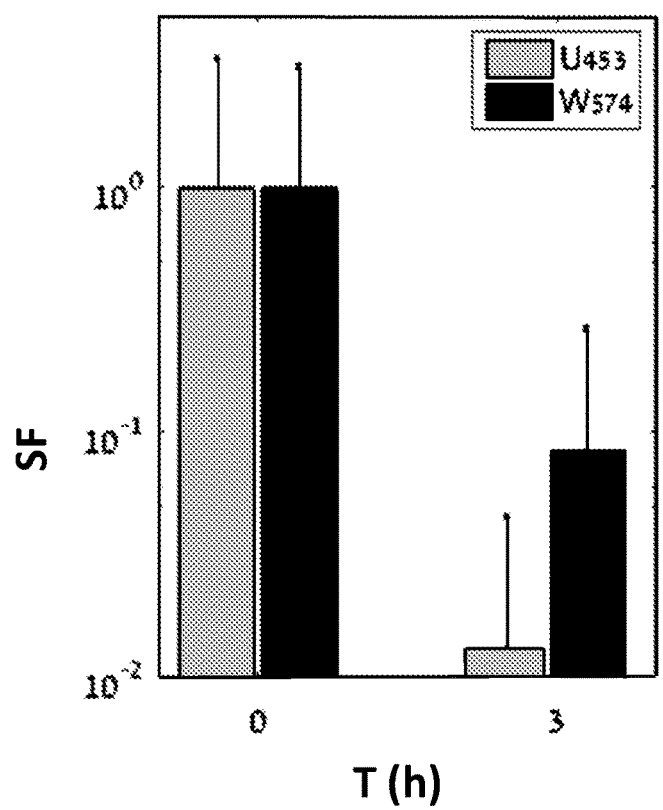

FIG. 8E shows the survival fraction in liquid culture of W574 (bright) and U453 (dark) under ertapenem (10 microgram/ml).

Abbreviations: SF (survival fraction); T (time); h (hours).

FIG. 9A-9F show time-lapse microscopy of E. coli strains U453 and W574.

FIG. 9A-9C: U453.

FIG. 9D-9F: W574.

(Bar: 3 μm, Time: hours:min)

FIG. 10A-10E show the effects of ampicillin and kanamycin on tbl3a strain.

Figures 10A, 10B:
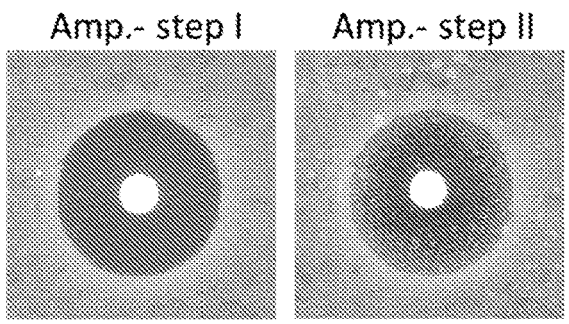

FIG. 10A: tbl3a growth after exposure to ampicillin (10 μg) in step I of the TDtest.

FIG. 10B: tbl3a growth following exposure to ampicillin, after step II of the TDtest.

Figures 10C, 10D:
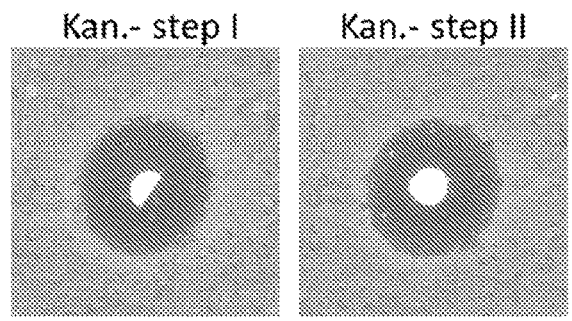

FIG. 10C: tbl3a growth after exposure to kanamycin (15 μg) in step I of the TDtest.

FIG. 10D: tbl3a growth following exposure to kanamycin, after step II of the TDtest.

Figure 10E:
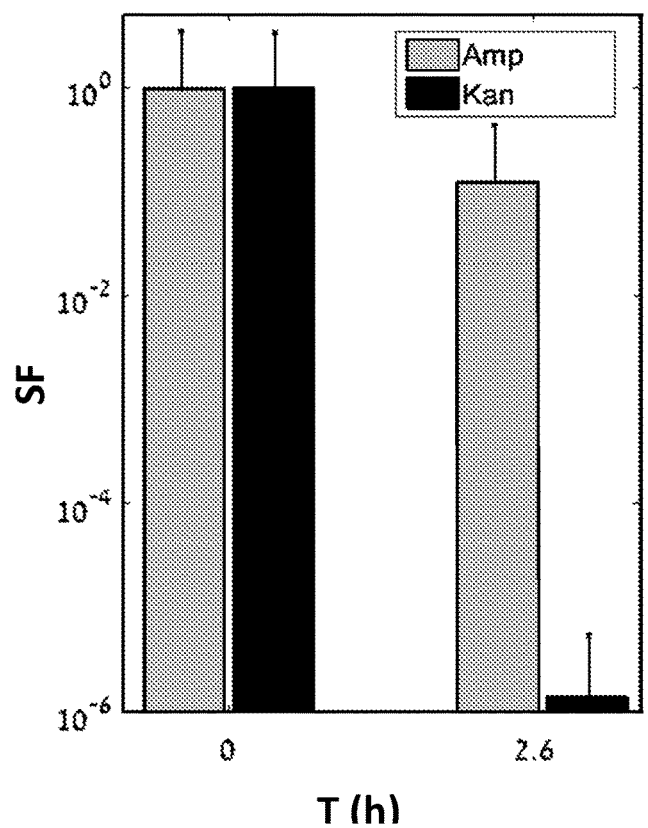

FIG. 10E: Time-kill curves of tbl3a in kanamycin 100 microgram/ml (bright) and ampicillin 100 microgram/ml (dark).

Abbreviations: Amp (ampicillin); Kan (kanamycin); SF (survival fraction); T (time); h (hours).

Figures 11A, 11B:
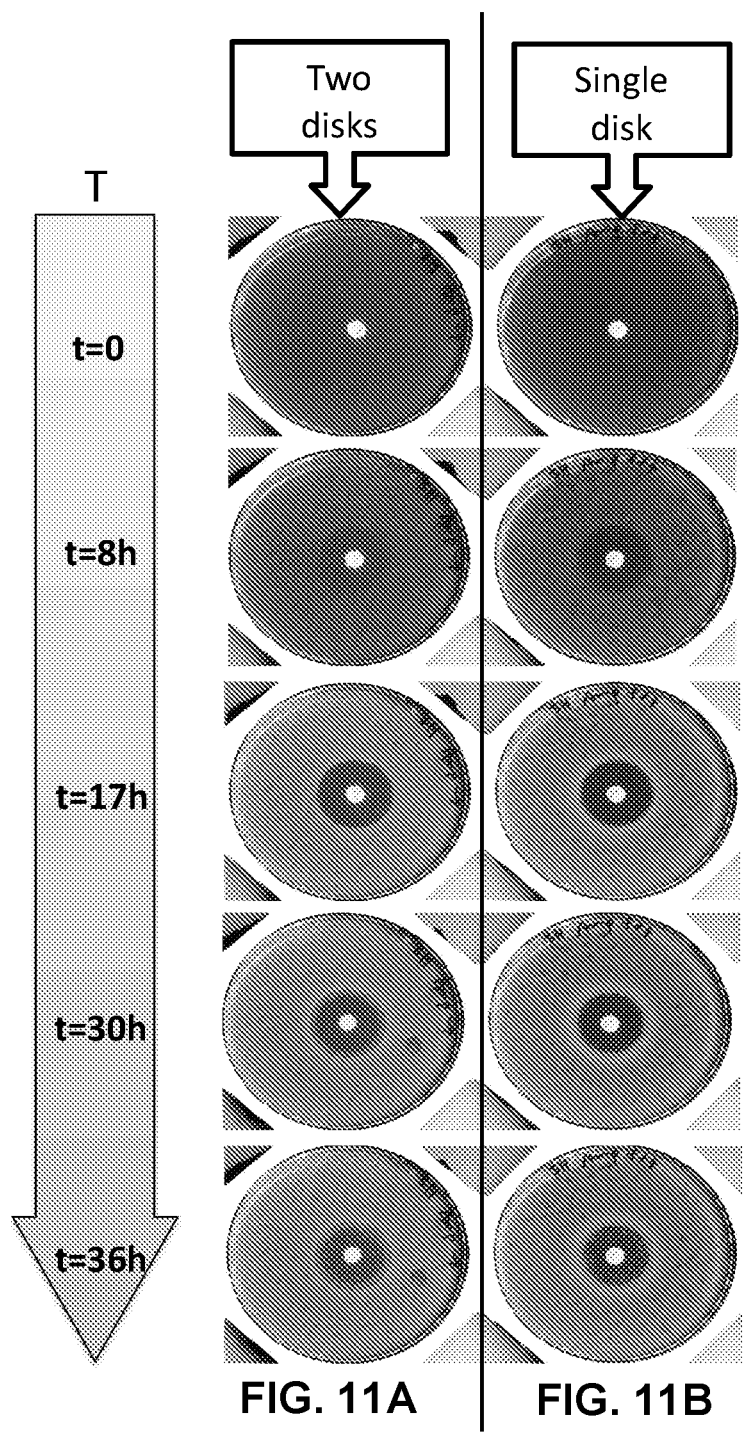

FIG. 11A-11B show the growth of tolerant bacteria (tbl3a) at several time points in response to two different disks according to the TDtest. In both plates, the bacterial colonies are well seen after 36 hours.

FIG. 11A shows the "two steps" procedure, meaning that the antibiotic disk, comprising ampicillin was replaced by a glucose disk after 18 hours.

FIG. 11B shows a "single disk TDtest", in which the disk placed at the beginning of the experiment (t=0) comprises both an antibiotic and glucose.

Abbreviations: T or t (time); h (hours).

FIG. 12A-12E show different options for the TDtest disk.

Figure 12A:
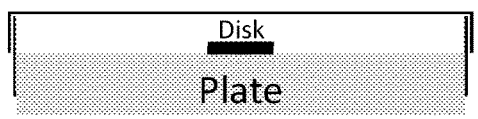

FIG. 12A is shows the disk placed on top of the microorganism growth plate, after plating the microorganism.

Figure 12B:
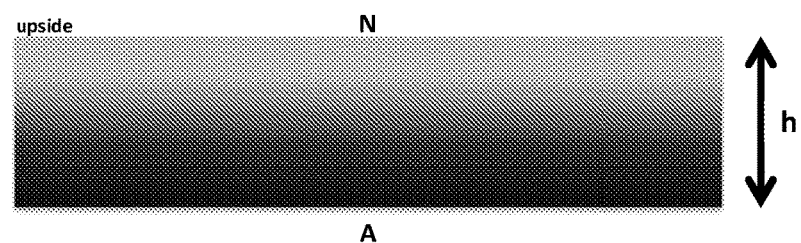

FIG. 12B depicts a two phase diffusion disk having initial spatial separation, wherein high concentration of antibiotic on the lower side, and high concentration of nutrients on the upper side. The high (h) of the disk defines different TDtest duration.

Figure 12C:
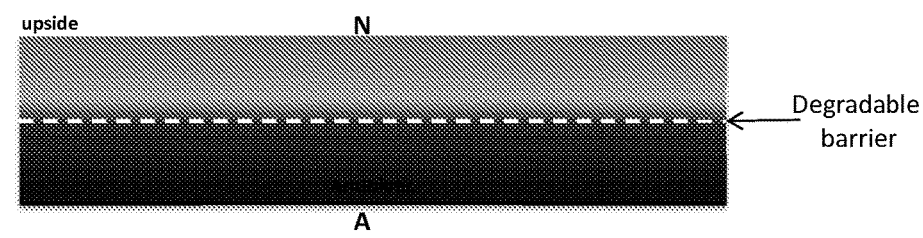

FIG. 12C depicts a two phase diffusion disk having initial spatial separation with degradable barrier.

Figure 12D:
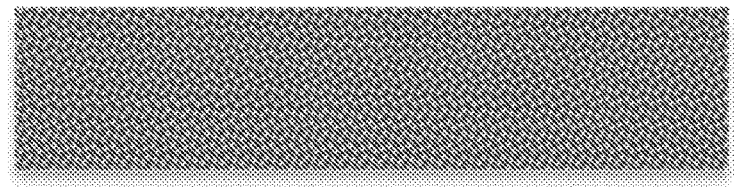

FIG. 12D depicts a two phase availability disk having an initial uniform mix of the antimicrobial agent and the nutrient, but the nutrients are in larger particles, or bind to larger particles, and therefore have a lower diffusion coefficient.

Figure 12E:
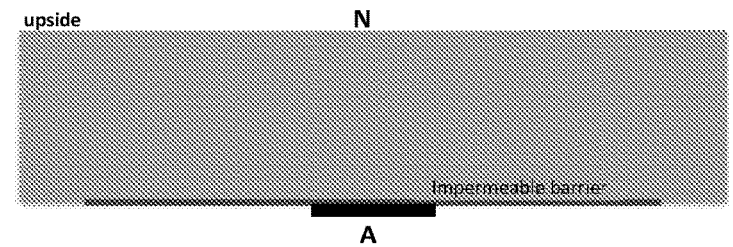

FIG. 12E shows a two phase availability disk impregnated with nutrients, and the antibiotic is placed below an impermeable barrier.

Abbreviations: N (nutrients); A (antimicrobial agent).

Figure 13A:
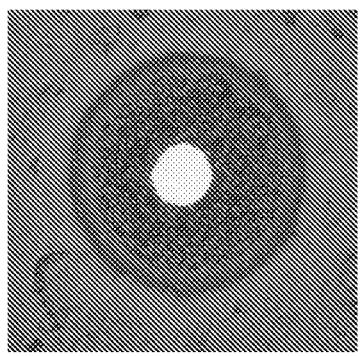
Figure 13B:
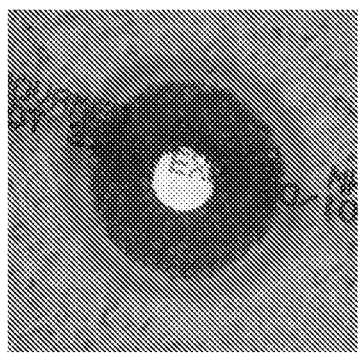
Figure 13C:
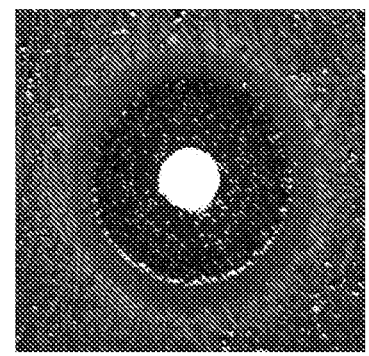

FIG. 13A-13C show TDtest performed on three different growth media. The results are shown after the second step of TDtest examining the effect of ampicillin on tbl5a.

FIG. 13A is a LB agar plate.

FIG. 13B is a Mueller-Hinton agar plate.

FIG. 13C is a Mueller-Hinton+5% Blood agar plate.

This bacterial strain, tbl5a, is detected as having medium tolerance on all media.

FIG. 14A-14I show tbl3a bacterial colonies inside the growth inhibition zone after treatment with 2.5 microgram imipenem.

FIG. 14A shows the growth inhibition zone after the first step of the TDtest (exposure to imipenem antibiotic only). The dashed lines mark the diameter of the inhibition zone.

FIG. 14B shows the growth inhibition zone after the second step of the TDtest (replacement of the antibiotic disk with a glucose-containing disk). Appearance of colonies inside the inhibition zone occurs after a few hours and indicates tolerant/persistent bacteria.

FIG. 14C: a mixture of 5-10 colonies that grew inside the inhibition zone of the plate of FIG. 14B were picked and retested to imipenem. The dashed lines mark the diameter of the inhibition zone, which is the same as observed in FIG. 14A.

Figure 14D:
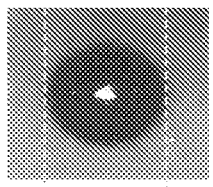
Figure 14E:
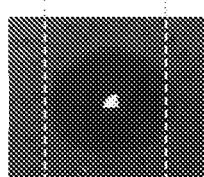
Figure 14F:
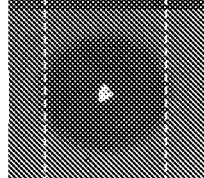
Figure 14G:
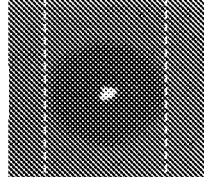
Figure 14H:
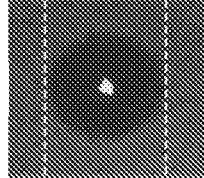
Figure 14I:
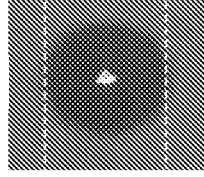

FIG. 14D is a duplicate of FIG. 14A.

FIG. 14E-14I show the results of resuspension and retest of 5 different colonies taken from the inhibition zone of the plate shown in FIG. 14B. The inhibition zone has the same diameter as in FIG. 14A.

FIG. 15A-15I show tbl3a bacterial colonies inside the growth inhibition zone after treatment with 10 microgram ampicillin.

FIG. 15A shows the growth inhibition zone after the first step of the TDtest (exposure to ampicillin only). The dashed lines mark the diameter of the inhibition zone.

FIG. 15B shows the growth inhibition zone after the second step of the TDtest (replacement of the antibiotic disk with a glucose-containing disk). Appearance of colonies inside the inhibition zone occurs after a few hours and indicates tolerant/persistent bacteria.

FIG. 15C: a mixture of 5-10 colonies that grew inside the inhibition zone of the plate of FIG. 15B were picked and retested to imipenem. The dashed lines mark the diameter of the inhibition zone, which is the same as observed in FIG. 15A.

Figure 15D:
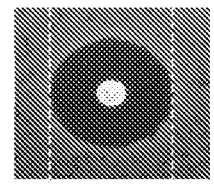
Figure 15E:
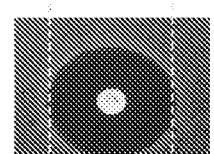
Figure 15F:
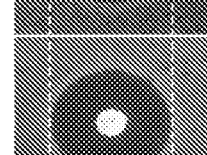
Figure 15G:
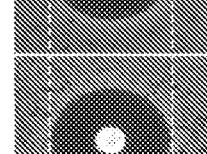
Figure 15H:
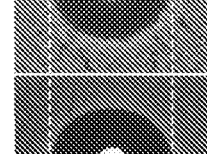
Figure 15I:
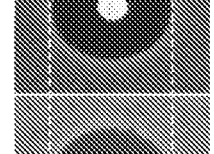

FIG. 15D is a duplicate of FIG. 15A.

FIG. 15E-15I show the results of resuspension and retest of 5 different colonies taken from the inhibition zone of the plate shown in FIG. 15B. The inhibition zone has the same diameter as in FIG. 15A.

DETAILED DESCRIPTION OF THE INVENTION

The present invention concerns a significant upgrade to the standard disk diffusion antibiotic survival test. The novel assay, termed Tolerance Diffusion test (TDtest) enables determining whether a microorganism is susceptible, resistant or tolerant to an antimicrobial agent. This information is important for tailoring treatment regiments against pathogenic microorganisms, and to better adjust clinical treatment protocols.

The microorganism tested according to the present invention is isolated from a sample obtained from a human subject, an animal subject, an environmental source or a food source, originating, for example, from the food industry.

The term "microorganism" refers to any type of microorganism that is tested for susceptibility or resistance to antimicrobial agents or biocides, such as antibiotics and antiseptics. This term includes bacteria and other microorganisms such as a fungus, a yeast, a parasite, etc.

The term "sample" includes any specimen obtained from a human or animal subject that requires testing for susceptibility, resistance, tolerance and any other response to antimicrobial agents, such as antibiotics, and includes blood, plasma, urine, sperm, milk, mucosal samples, throat swabs, ear swabs, vaginal swabs, cerebro-spinal fluid, tissue samples, swabs from sores or skin. This term also relates to microbiological cultures held and reproduced under laboratory conditions.

The terms "antimicrobial agent" and "antibiotic" refer to any type of compound, or combination of compounds that is used to treat bacterial or fungal or any other microorganism infection, by any mechanism, or more generally, any substance that results in the killing of microorganisms whether in an infection or in the environment, in food processing or on general surfaces. These include any antibiotics, antifungal, biocide, germicides, antiseptics, disinfectants and preservative.

The terms "growth boosting agent" or "growth promoting factor", which are used interchangeably throughout the description, refer to any compound or combination of compounds that promote the growth of microorganisms in the inhibition zone, any substance that would provide food such as sugars, amino acids, peptides, proteins, or alter the conditions by changing the pH such as acids or bases, or any resuscitation factor that alters the metabolism of microorganisms, or any factor that would result in a more rapid degradation of the antimicrobial compounds.

The term "tolerance" as used herein refers to microorganisms that survive under a transient antimicrobial treatment without a measurable increase in MIC. Typical observations of tolerance are related to a dormant, non-growing stage, which require longer periods of exposure to the antimicrobial agent than susceptible microorganism in order to be eliminated.

The term "persistence" as used herein refers to a subpopulation of microorganisms that is able to survive antimicrobial treatment. This phenomenon is caused by a heterogeneous response of a clonal bacterial population to the antimicrobial agent.

In one aspect, the present invention provides a detection method and a kit for evaluating tolerance or persistence levels of bacterial isolates in the clinic.

Figure 1A:
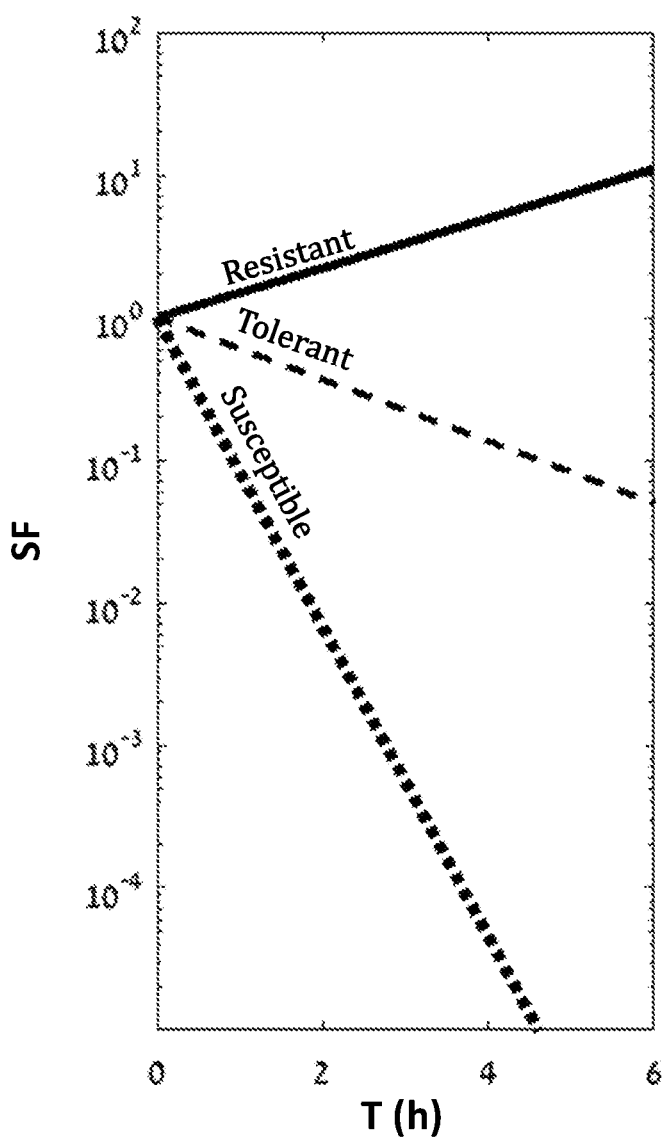
FIG. 1A-1D show different responses of bacteria to antibiotics.

In the "disk diffusion antibiotic survival testing" the antibiotic gradient on the plate is set while the bacteria are growing on the plate. Therefore, the size of the clear inhibition zone around the disk is the interplay between the diffusion rate of the antibiotic and the growth rate of the bacteria. After an "overnight" incubation, the antibiotic concentration near the disk may drop below the MIC value by diffusion in the plate. However, by this time, the nutrients are depleted by the bacteria that grew in the clear zone periphery. Consequently, the small population of tolerant bacteria which have survived the bactericidal antibiotic within the inhibitory zone would not be able to reproduce and form visible colonies, because nutrients are depleted by the time the antibiotic level drops below the MIC. FIG. 1A is a schematic demonstration of the survival fraction of susceptible, tolerant and resistant bacterial strains in response to an antibiotic.

Figure 1B:
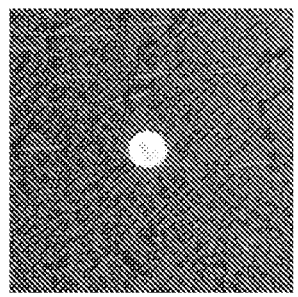
Figure 1C:
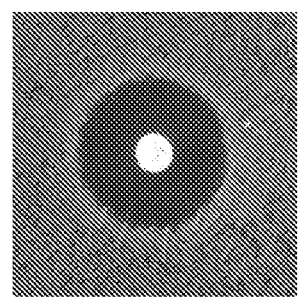
Figure 1D:
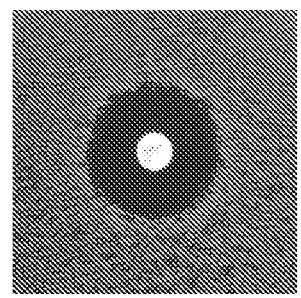

It should be noted that tolerant bacterial cultures may contain large fractions of non-growing or slower growing bacteria. Those bacteria are alive, and may survive the antibiotic treatment, even in the high antibiotic concentration zone close to the disk. However, the lack of nutrients in the growing medium may prevent them from reproducing and forming visible colonies, leading to the failure to detect their presence in the sample when using standard antibiotic sensitivity tests. Typical response to antibiotic treatment is shown in FIG. 1B-1D. FIG. 1B shows the results obtained by standard Disk diffusion assay of a resistant bacterial strain. No inhibition zone is visible. FIG. 1C shows the results obtained by standard Disk diffusion assay of a tolerant bacterial strain (tbl3a). A growth inhibition zone around the antibiotics disk is visible. FIG. 1D shows the results obtained by standard Disk diffusion assay for a susceptible strain (KLY) having the same MIC as the tolerant strain shown in FIG. 1C. A growth inhibition zone around the antibiotics disk is visible. Accordingly, the standard diffusion assay does not discriminate between tolerant and susceptible bacteria. Depending on the amount of antibiotic in the disk, after overnight incubation, the antibiotic concentration in the inhibition zone can drop below the MIC (FIG. 2A). However, by this time, the nutrients have diffused in the plate and are depleted by the bacteria that grew in the inhibition zone periphery (FIG. 2B). Tolerant bacteria that have survived the transient exposure to the antibiotic would not be detected because of the lack of nutrients supporting their visible growth.

The inventors have identified that what prevents surviving bacteria from growing after the typical overnight incubation using commercial disks according to the disk diffusion test are two factors. First, the antibiotic concentration in most commercial disks is too high and therefore the concentration in the culture plate does not drop below the MIC. Second, even when the antibiotic concentration is low enough to fall below the MIC after overnight incubation, the surviving bacteria are depleted of nutrients by that time and are not be able to grow. Therefore, the standard disk diffusion test does not detect tolerant bacteria.

The present invention represents a significant improvement of the Kirby-Bauer disk diffusion test. The first part of the method according to the invention, similar to the standard disk diffusion test, detects whether the bacterial isolate grown is resistant to one or more tested antimicrobial agents. For bacterial strains that do not manifest resistance, a second step of the assay determines whether the bacteria are susceptible or tolerant to the tested antimicrobial agents, and further evaluates the level of tolerance.

The method of the invention comprises two steps. In step I, the examined microorganism sample is inoculated on plates, exposed to one or standard antibiotic susceptibility disks, each containing a single concentration of the tested antibiotic, or alternatively, one or more disks comprising lower concentrations of antibiotics or one or more strips comprising several concentrations of the antibiotic, and then incubated for a period of time, such as overnight. In step II, after a pre-defined delay periods, such as an overnight incubation, the plate is exposed to at least one "growth boosting" factors, such as nutrients and/or growth factors, at the location of the antibiotic disks or strips, i.e., at the center of the antibiotic disk or the inhibition zone, and the plate is incubated for another pre-defined delay period, such as overnight. Finally, the plate is inspected to detect microorganism existence within the inhibition zone. The lack of growth in the inhibition zone indicates that the microorganism is susceptible to the tested antimicrobial agent. Visible colonies within the zone indicate that the microorganism is tolerant to the tested antimicrobial agent. The results of such an approach can be seen in FIG. 3D, where the addition of a "growth boosting" disk comprising glucose reveals the presence of tolerant bacteria that survived the antibiotic treatment.

Thus, according to one aspect, the present invention relates to a method for identifying the susceptibility, tolerance or resistance of a microorganism to one or more antimicrobial agent, comprising:
 a. inoculating a microorganism isolated from a sample on a microorganism growth plate;
 b. exposing the surface of the plate to one or more antimicrobial agents;
 c. incubating the plate for a first period of time;
 d. exposing the surface of the plate to at least one growth promoting agent;
 e. incubating the plate for a second period of time;
 f. observing the growth pattern of said microorganism on said plate;

wherein the susceptibility, tolerance or resistance of said microorganism to said antimicrobial agent is determined according to the presence (or absence) and growth pattern within the inhibition zone.

According to one embodiment of the invention, the microorganism is selected from bacteria, fungi, yeast and parasites. In one specific embodiment the microorganism is a bacterium.

The microorganism of the invention is isolated from a human, animal or environmental sample. Alternatively, the microorganism is a laboratory strain.

The microorganism obtained from the sample is suspended to approximately $10^7$-$10^8$ bacteria/ml, and 0.1 ml of the suspension are plated on solid medium microorganism growth plate.

The microorganism growth plate according to the invention may be any suitable surface supporting the growth of microorganisms. According to one embodiment, said surface is a standard growth plate, such as a 9 cm diameter Petri dish.

The growth medium in the plate according to the invention is any suitable medium for the growth of microorganism. According to one embodiment of the invention, the medium is selected from Lysogeny broth (LB), Mueller-Hinton or Mueller-Hinton+blood agar.

The antimicrobial agent according to the invention is any known and acceptable compound suitable for the killing or inhibiting the growth of a microorganism. According to one embodiment of the invention, the antimicrobial agent is an antibiotic, an antibacterial agent, an antiseptic or an antifungal agent. The antibiotic according to the invention is one or more of a beta-lactam antibiotic, a cepheme antibiotic, a glycopeptide antibiotic, an aminoglycoside antibiotic, a macrolide antibiotic, a tetracycline antibiotic, and a quinolone antibiotic. According to a specific embodiment, the beta-lactam antibiotic is selected from penicillins, uredopenicillins, synthetics, carbapenems and beta-lactam/inhibitors. According to another specific embodiment, the cepheme antibiotic is selected from cephalosporins generations I to IV, and carbacephems. Also, the one or more antimicrobial agent can comprise one or more of sulfa agents and derivatives, chloramphenicol, dindamycin, nitrofurantoins, polymyxins and chemical agents. Specific examples of suitable antibiotics are ciprofloxacin, imipenem, gentamicin, cefazolin, rifampicin and colistin.

Each antimicrobial agent according to the present invention are provided by a carrier, i.e., a disk containing a single concentration, or a strip (also designated as "slip"), containing several concentrations. The disks or strips are placed on the surface of the plate inoculated with the examined microorganism, and the antimicrobial agents start to diffuse through the growth medium, forming a concentration gradient. The carrier material is a plastic, a polymer, a hydrogel or a membrane (such as paper). A simple non-limiting example of a carrier according to the invention is a filter paper.

Thus, according to one embodiment of the invention, instead of using a standard disk with a homogenous concentration of antimicrobial agent, a reagent strip with varying concentrations of the active agent may be used. The reagent strip has a predefined gradient of antibiotic for the determination of precise MIC values of a wide range of antimicrobial agents against different microorganism groups.

When the disk or strip is applied to the surface of a microorganism growth plate inoculated with the examined strain, there is a release of the antimicrobial gradient from the carrier to the solid medium (i.e., agar) to form a stable and continuous gradient beneath and in the immediate vicinity of the disk or strip.

Accordingly, the first step of the method of the invention comprises the standard implantation of a microorganism, optionally isolated from a sample, on a microorganism growth plate, such as a standard agar plate, and the placement of antimicrobial impregnated disks or strips on the growth medium.

The amount of the antimicrobial agent or antibiotic in the disk or strip is important, and should be adjusted to fall below the MIC of the microorganism after the time set by the assay. For example, an amount of 10 microgram of kanamycin results in an inhibition zone of approximately 2 cm diameter for a strain with an MIC of 4 microgram/ml. After 18 hours, the kanamycin concentration within the inhibition zone starts falling below the MIC. Alternatively, the amount of antimicrobial agent diffusing into the plate can be adjusted by the use an antibiotic deactivating agent during the first incubation step, such as absorbing agents, heat or specific enzymes.

It should be noted that the first stage of the method according to the invention can be identical to the standard disk diffusion antibiotic sensitivity testing, as done today. However, changes in the concentrations of the antibiotics used may be required to insure that each chosen concentration falls under the MIC of the tested microorganism.

After the disk or strip are placed on the surface of the plate inoculated with the examined microorganism, there is need to wait for a first predefined period of time so that the one or more antimicrobial agent, or antibiotic, can diffuse away. If the microorganism is not resistant to the antimicrobial agent, a clear inhibition zone will be formed around the disk or strip. Typically, the pre-defined period of time is between about 6 and about 30 hours, specifically between 10 and 24 hours, for example 18 hours. The incubation time is predetermined depending on the diffusion constant of the antibiotic and the growth dynamics of the bacteria. Preference is given to the shortest possible time, in order to reduce the total time of the assay.

After the first incubation period, the plate is exposed to at least one growth promoting agent (also referred to herein as growth boosting factor).

The delayed exposure of the plate and microorganisms on it to the growth promoting agent may be achieved by applying the growth promoting agent to the plate after the first pre-defined incubation. Alternatively, the growth promoting agent is applied at the same time as the antimicrobial impregnated disks or strips, but is designed so the at the growth promoting agent is released or diffuses in a slower rate than the antimicrobial agent, for example only after the first pre-defined incubation.

Accordingly, the growth boosting agent is added as a separate disk after a first period of time (i.e., 18 hours). Alternatively, the growth boosting agent is present in the antibiotic disk, in a form that diffuses slower than the antibiotic. Still alternatively, the growth boosting agent is present in the growth medium (i.e. agar) in the plate, in a form that is released slower than the nutrients present in typical plates.

The growth promoting agent may be a nutrient source, such as a sugar, an amino acid, a lipid, a fatty acid, a mineral, and a vitamin, or a factor that promotes growth, such as a pH changing chemical, for example an acid, or a base or a buffering agent, an antibiotic degrading agent or an antibiotic deactivating agent, for example a beta-lactamase, an antibiotic inhibitor or an activator of intrinsic resistance factors in the microorganism (i.e. bacteria), or any combination of two or more factors or agents of the above. These factors promote the growth of tolerant microorganism, if present in the sample, in the inhibition zone.

In accordance with a specific embodiment of the invention, the growth boosting factor is a nutrient source, specifically a sugar, and more specifically glucose.

The total amount of growth boosting factor per disk varies according to the nature of the factor. In the case of glucose, each disk contains between 0.1 mg to 4 mg. The optimal amount for *E. coli* is found to be 2 mg/disk. Different amounts may be required for other microorganisms or bacterial strains.

According to one embodiment of the invention, the growth promoting agent is placed on the plate by a disk. The growth boosting factor disk may be a polymeric, a hydrogel or a membrane (such as paper) material, impregnated with the factor. A simple non-limiting example of the disk according to the invention is a filter paper carrying on it a dried solution of at least one nutrient, such as glucose.

According to another embodiment, the growth promoting agent is applied directly onto the plate, i.e. by dripping a solution.

After the growth boosting factor is applied, the microorganism growth plate is incubated for a predefined period of time of between about 5 and about 30 hours, specifically between 6 and 24 hours, more specifically between 10 to 18 hours, for example 18 hours.

Finally, the plate is viewed and examined either manually or by an automatic inspection and analyzing system or machine.

In one embodiment of the invention, the antimicrobial agent and the growth promoting agent are provided to the microbial culture separately. The addition of the growth promoting agent after the first incubation period, according to step II of the assay, is performed by replacing the antibiotic disk or strip by a disk comprising at least one growth promoting agent, or by removing the antibiotic disk or strip and placing in the same location a solution of the growth promoting agent. Alternatively, a disk impregnated with at least one growth factor, or a solution of the factor is placed on top of the antibiotic disk or the strip.

According to another embodiment of the invention, the antimicrobial agent and the growth boosting factor are present in a single disk, designated as a "two phase diffusion/availability disk". The composition and/or structure of the disk allow the diffusion of the antimicrobial agents first, and only later, after a delay, the diffusion of the growth boosting factor throughout the growth plate. Alternatively, both the antimicrobial agent and the growth boosting factor diffuse at the same rate, but the growth boosting factor is provided initially in a form that is unavailable to the microorganism (in a degradable particle, in the form of a "progrowth boosting factor" that is metabolically unavailable), and only after said first pre-defined delay, the growth booster is released from the particle or converted from the "pro" form to a metabolically available form. One example of the above technique is a growth boosting factor that is activated by the pH change induced by the growth of the bacteria outside the inhibition zone.

In one embodiment, the two phase diffusion/availability disk comprises the antimicrobial agents and the growth boosting factors in two separate regions or layers, thereby the growth boosting factor is separated from the surface of the growth plate by a degradable barrier. When the two phase diffusion/availability disk is applied to the plate, the antimicrobial agent starts to diffuse immediately, while the degradable barrier maintains the growth boosting factors within the disk. The barrier disintegrates after the first predefined period of time, namely, after the diffusion of the antibiotic is over, and only then the factors diffuse throughout the plate. In this case, the growth boosting factor side of the disk should be marked, and placed "face up" on the plate. The use of different disks comprising the same antibiotic but release the growth promoting agents in variable rates enables the evaluation of the level of tolerance of the microorganism to the tested antibiotic. The release rate of the growth boosting factors from the disk is controlled by the material composing the degradable barrier and its properties such as its thickness and permeability.

In another embodiment, the two phase diffusion/availability disk is composed of two types of carrier materials. The one holding the antimicrobial agents (antibiotics) allows fast diffusion therefrom, and accordingly the diffusion starts immediately upon contact with the growth plate. The other carrier material is present in a different region of the disk and holds the growth boosting factor, which starts to diffuse only after a delay. The release rate of the factors from the disk is controlled by the properties of the carrier material, for example, the pore size of the carrier material, or because the carrier material requires activation (i.e., by swelling, degradation, etc.) before releasing the carried nutrients.

By yet another embodiment, the antimicrobial agents and the growth boosting factors are present on the same disk in a "two phase release" manner. In one option, the antimicrobial and the factor both diffuse from the disk immediately upon contact with the plate, but the growth boosting factor is released in a slower rate and has a significantly smaller diffusion constant compared to the antimicrobial agent, for example due to its larger size. In another option, the term "two phase diffusion manner" means that antimicrobial agent and the growth boosting factor both diffuse from the disk from the very start, immediately upon contact with the plate, but the diffusion rate of the growth boosting factor is slower, due to its larger amount or its initial spatial location in the disk, leading to a concentration around the disk sufficient for microorganism consumption only after several hours.

According to a further embodiment, the antimicrobial agents and the growth boosting factors are present on the same disk in a "two phase availability" manner, meaning that the antimicrobial and the growth boosting factor both diffuse from the disk at similar rates from the very start, immediately upon contact with the plate. However, the antibiotics are in a form that is immediately available to the microorganisms' cells consumption, and the growth boosting factors are in a form that becomes available to the microorganisms' cells only after a delay. Accordingly, the growth boosting factors are present in aggregates or crystals that disintegrate after a pre-defined delay. Alternatively, the growth boosting factors are present in degradable nanoparticle, nanocapsules, or liposomes, optionally polymeric, which disintegrate after the first predefined period of time, thereby making the factors available to the microorganism present on the plate.

Different TDtest disks according to the present invention are schematically demonstrated in FIG. 12. A two phase diffusion disk having an initial spatial separation is shown in FIG. 12B. High concentration of antibiotic on the lower side, and high concentration of nutrients on the upper side. After the wetting, the nutrient start diffusing toward the plate. The height of the disk may define different TDtest durations (see FIG. 11 for results from such a disk). A different two phase diffusion disk, having an initial spatial separation with degradable barrier is shown in FIG. 12C. In this case, the degradation of the barrier after the wetting starts the diffusion of the nutrients.

A two phase availability disk is shown in FIG. 12D. This disk comprises a uniform mix of the antibiotic and the nutrient, but the nutrients are in larger particles, or bind to larger particles, and therefore have a lower diffusion coefficient, and diffuse slower. Note that this disk has no orientation. Another two phase availability disk is shown in FIG. 12E. This disk is impregnated with nutrients, and the antibiotic is placed below an impermeable barrier. The antibiotic diffusion pattern is similar to diffusion from a point source and the nutrients slowly diffuse from the periphery of the disk.

The inspection of the microorganism growth pattern obtained by the method of the invention allows the identification of the type of response of the microorganism to each tested antimicrobial agent, namely resistance, tolerance, and susceptibility. Bacteria susceptible to the tested antibiotic are visualized by a clear zone around the disk, optionally with sharp edges and no bacterial growth in the inner zone (FIG. 3B). Tolerant bacteria are visualized by a clear bacteria growth inhibition zone with several colonies present in the inner periphery of the zone after the second incubation period, as shown in FIG. 3D, and FIGS. 6B-6C. Resistant or heteroresistant bacteria are visualized by a growth of bacteria close to the disk already after the first incubation period, namely in the first observation period (FIG. 1B).

The method according to the invention also detects subpopulations of tolerant bacteria, namely persistent bacteria. Persistent bacteria are visualized, similarly to tolerant bacteria, by a clear bacteria growth inhibition zone with several colonies present in the inner periphery of the zone after the second incubation period, as shown in FIG. 6E.

Moreover, the method of the invention enables the identification and designation of levels of tolerance and persistence, according to the number of colonies present in the inhibition zone after the second incubation period. "Low tolerance" is 0-10 colonies in the inhibition zone, "medium tolerance" is 10 to a few hundred colonies in the inhibition zone, and "high tolerance" is a bacterial lawn covering the inhibition zone. (FIG. 6A, FIG. 6B and FIG. 6C, respectively).

Furthermore, the tolerant bacteria detected with the Tolerance Diffusion test (TDtest) according to the invention are also distinct from heteroresistance, which may also result in colonies inside the inhibition zone. Heteroresistance occurs when a sub-population of bacteria within a clone is actually growing within the disk diffusion assay inhibition zone. Therefore, heteroresistant colonies would appear already during the first step of the TDtest, despite an antibiotic concentration that is above the MIC of the majority population, whereas tolerant bacteria would appear only after the second step of the TDtest, once the antibiotic concentration in the zone decreases below MIC In another aspect, the present invention relates to a kit for identifying the susceptibility, tolerance or resistance of a microorganism to one or more antimicrobial agent.

In another aspect, the present invention relates to a kit for identifying the survival fraction of a microorganism to one or more antimicrobial agent.

The kit according to the invention comprises several disks for each antibiotic, containing different concentrations of the antibiotics for spanning the range of MIC below the breakpoint for resistance. Typically, the disks contain an amount of antibiotic that is between the amount present in commercial disk diffusion assays used for detecting "resistance", and two orders of magnitude below that amount. The range required for each assay depends on the antibiotic and its typical use in the clinic. For example, ertapenem disks for resistance assays contain 10 micrograms of ertapenem. Accordingly, a kit comprising ertapenem includes disks with 10, 3, 1, 0.3 and 0.1 micrograms of ertapenem. In one embodiment of the invention, the antimicrobial disks further contain at least one growth boosting agent. In another embodiment, the kit further comprises disks with the growth boosting agent, or alternatively a vial with the solution of the growth boosting agent. Optionally, the kit also comprises microorganism growth plates (i.e. agar) comprising at least one slow release growth boosting agents.

According to one embodiment of the invention, the kit comprises at least two disks or at least one disk and one strip. One disk, or the strip, is a carrier material impregnated with antimicrobial agents or antibiotics to be tested. The other disk is made of the same carrier material, or alternatively a different material, impregnated with a growth boosting factor as defined above. The kit may optionally include several carriers, each impregnated with different antimicrobial agents and/or different concentrations. Optionally, the kit further comprises instructions for use, stipulating that the antimicrobial agent (antibiotic) impregnated disk or strip should be placed first on the microorganism growth plate, and after the first predefined period of time, the growth boosting factor impregnated disk should be placed on the growth plate on top of the antimicrobial disk of strip, or alternatively should replace the antibiotics disk or strip.

According to another embodiment of the invention, the kit comprises at least one carrier (i.e., disk or strip) impregnated with an antimicrobial agent to be tested, and at least one vial containing a growth boosting factor solution. Optionally, the kit further comprises instructions for use, stipulating that the antimicrobial agent impregnated disk or strip should be placed first on the microorganism growth plate, and after the first predefined period of time, the growth boosting factor solution should be dripped on top of the antimicrobial disk of strip. Alternatively, after the first predefined period of time, the antibiotics disk or strip should be removed and then the growth boosting factor solution should be dripped at the same location.

According to another embodiment, the kit comprises a single disk having two phase diffusion rates, such that the antimicrobial agents (antibiotics) start diffusing immediately upon placing the disk on the growth plate, and the growth boosting factors start diffusing after the first pre-defined delay. As explained above, this is achieved by the presence of a barrier which disintegrates after a predefined period of time, or the presence of two types of carrier materials on the disk, one holding the antibiotics and allowing immediate diffusion therefrom, and the other holding the growth boosting factor, enabling delayed diffusion therefrom.

According to a further embodiment, the kit comprises a single disk having two phase availability of the antimicrobial agents (antibiotics) and the growth boosting factor. The antimicrobial agents are present in the disk in a form available for microorganism consumption immediately upon diffusion, while the growth boosting factors are present in a form that requires disintegration or degradation in order to be available to the microorganism. Examples of forms that need to be disintegrated and therefore delay the diffusion of the factors are aggregates or crystals or (low/high) pH activated reagents. Packaging of the factors in nanoparticles (for example polymeric), nanocapsules, or liposomes, which required degradation, delays the release the nutrients and/or growth factors until after the first pre-defined period of time.

In summary, the present invention provides an efficient and cost-effective assay for detecting increased survival of micro-organisms to various agents, thus identifying tolerant and persistent strains. In addition to its potential benefit for the clinical setting, the methods and kits of the invention enable more rapid screens for compounds or combinations that are potent against tolerant and persistent bacteria and speed up drug development. Finally, the simplicity and low cost of the technique of the invention may be used in third world country to characterize strains and classify them according to the rapidity of their killing under several antibiotics.

Disclosed and described, it is to be understood that this invention is not limited to the particular examples and methods steps disclosed herein as they may vary somewhat. It is also to be understood that the terminology used herein is used for the purpose of describing particular embodiments only and not intended to be limiting since the scope of the present invention will be limited only by the appended claims.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The term "optional" or "optionally" as used herein means that a subsequently described event or circumstance may, but need not, occur, and that the description includes instances where the event or circumstance occurs and instances in which it does not.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Materials and Methods
Media and Reagents
Growth medium used was LB Lennox (LBL). All other chemicals, unless stated otherwise, were purchased from Sigma Chemical Co.
Antibiotics used: Ampicillin stock solution 100 mg/ml in DDW was kept as single use aliquots. Ertapenem (MERCK) stock solution 20 mg/ml in DDW. Kanamycin stock solution 30 mg/ml in DDW. All antibiotic stock solutions were kept at −20° C.
Antibiotic disks and content: ampicillin 10 micrograms (Bio-rad and OXOID), kanamycin 15 micrograms (Bio-rad), imipenem 2.5 micrograms (OXOID), gentamicin (OXOID), cefazolin 7.5 micrograms (OXOID), colistin sulfate 10 micrograms (OXOID). Self-made: ciprofloxacin 0.1 micrograms, ertapenem 0.25 mg.

Glucose (D-glucose) was purchased from JT Baker.

TABLE 1

Bacterial strains

| Strain | Relevant characteristics |
|---|---|
| W574 | E. coli clinical strain |
| U453 | E. coli clinical strain |
| B340 | E. cloacae clinical strain |
| KLY | E. coli K-12 strain with YFP-Cam cassette |
| tbl3a | High tolerance strain, evolved in vitro from KLY under transient antibiotic exposures of 3 hours (vapB mutant) |
| tbl5 a | High tolerance strain, evolved in vitro from KLY under transient antibiotic exposures of 5 hours (metG mutant) |
| MGY | MG1655 with YFP-Cam cassette |
| MGHY | P1 transduction of high persistence hipA7 mutation from HM22 (tetracycline selection) into MGY |

Preparation of Discs

Filter paper (Whatman, #1), used as the carrier material, was cut in circles of 6 mm diameter, sterilized by autoclave and impregnated with either 5 microliter of a 40% sterile glucose solution for glucose disks, or 4-10 microl of antibiotic solution, according to final required amount for antibiotic disks, and left to dry at room temperature. Alternatively, commercial disks were cut in half or quarter to reduce the amount of impregnated solution.

The exact amount of antibiotics used for the preparation of the discs is not important, as long as it is high enough to create a large inhibition zone, and low enough to allow the concentration of the antibiotics to fall below the MIC after 18 hours. For example, ampicillin MIC is around 4 microgram/ml in many species, therefore, the amount used to prepare ampicillin discs was between 5 to 10 microgram/disc.

2 Disc Test (TDtest) Procedure

The TDtest consists of two steps:

Step I—Incubation with Antibiotics:

Circa $10^7$ bacteria at stationary phase (100 microliter) were plated on LBL nutrient agar plate. An antibiotic disc was placed on the agar. The plate with the antibiotic disc was incubated for at least 4 hours and up to 30 hours, preferably about 18 hours at 37° C.

The amount of antibiotics in each disk was adjusted to reach a concentration below the MIC in the inhibition zone after an overnight incubation at 37° C. Many commercial disks contain antibiotics in amounts that are too high for the concentration to fall below the MIC after this time. When this was the case, custom disks were prepared as specified herein below.

In cases where high tolerance was detected by a lawn of bacteria in the inhibition zone, the test was repeated with a lower inoculum, for example circa $10^6$ stationary phase bacteria.

Step II—Incubation with Nutrient:

This step was carried out in one of the following protocols:

a. The antibiotic disk was replaced with a nutrient (i.e. 2 mg glucose) disk at the end of the antibiotic incubation time. The plate was incubated again for an additional overnight (at least 5 hours and up to 24 hours, preferably about 18 hours) at 37° C.

b. Nutrient solution (i.e., 2 mg glucose, or 5 microliter of 40% glucose solution) was added directly on the antibiotic disk, instead of replacing it.

c. Two phases disk was prepared, by impregnating 6 mg glucose on the upper side of the disk.

After the completion of the above steps, the growth of the bacteria was visually inspected.

Time-Kill Experiments

Overnight bacterial cultures were diluted 1:100 in fresh medium containing antibiotic and incubated at 37° C. for designated time. Bacterial survival was determined by the most probable number-counting method (MPN), as described in Hurley, M. A. & Roscoe, M. E. Automated Statistical-Analysis of Microbial Enumeration by Dilution Series. J Appl. Bacteriol. 55:159-164 (1983).

Time-Lapse Microscopy

A Polydimethylsiloxane (PDMS) square mold was cut out of cured Sylgard 184 (Dow Corning) layer (thickness: about 3 mm). The mold was filled with melted LBL agarose 1.5%. Bacteria (about 5 microliter of 1:10 from stationary phase) were put on a coverslip (#1.5) and covered with the solidified LB-agarose inside the PDMS mold. The whole chamber was sealed with another coverslip to avoid agarose drying. The PDMS chambers were monitored using a Leica DMIRBE inverted microscope system with incubator box (Life Imaging Systems) at 37° C., automated stage and shutters. Autofocus and image acquisition was done using Micro-Manager to control the microscope, stage, shutters and camera. Multiple locations were monitored in parallel for phase-contrast imaging. Images were acquired using a 100× oil objective and a CCD camera (Orca-ER; Hamamatsu).

Example 1

The Standard Disk-Diffusion Assay does not Detect Tolerant Bacteria

The Kirby-Bauer disk diffusion method is designed to identify resistant bacteria by creating a gradient of concentration around a disk impregnated with antibiotics. A resistant strain (FIG. 1B) will grow closer to the disk than a susceptible strain (FIG. 1D). However, applying the disk diffusion assay to a mutant strain that evolved under 3 hours of intermittent ampicillin exposures, and bearing tolerance mutation in the vapBC toxin-antitoxin module, did not reveal any reduction of the inhibition zone (FIG. 1C) when compared to the wild-type strain (FIG. 1D).

As clearly seen, the standard disk diffusion assay does not distinguish between susceptible and tolerant strains. Moreover, a slightly larger inhibition zone is often seen in tolerant strains because of delayed growth.

Example 2

The TDtest Detects and Discriminates Between Tolerant and Susceptible Bacteria

In order to understand better why the high tolerance does not appear in the standard disk-diffusion assay, one should think about both the diffusion of the antibiotic and bacterial growth on the plate. The size of the inhibition zone around the disk is set by the interplay between the diffusion rate of the antibiotic, the growth rate of the bacteria and the MIC.

The TDtest enables the detection of tolerant strains by tuning the antibiotic concentration in the disk and by overcoming the nutrient depletion that occurs in the Kirby-Bauer disk diffusion method. FIG. 2A shows a schematic plot of the diffusion dynamics during the TDtest in an arbitrary point in the inhibition zone. In this example, the antibiotic concentration drops to below the MIC after about 10 hours. Nutrients in the whole plate are consumed by the growing bacteria outside the inhibition zone (FIG. 2B, dotted line). Due to diffusion, nutrients in the inhibition zone are also depleted after several hours. The lack of nutrients prevents the re-growth of surviving tolerant bacteria, even though the antibiotics concentration is below the MIC. Replacing the antibiotic disk with the nutrient disk according to the TDtest allows re-growth and detection of the surviving tolerant bacteria (FIG. 2B, solid line).

The replacement of the empty antibiotic disk by a new disk impregnated with nutrients, according to step II of the TDtest, enables the surviving bacteria in the inhibition zone to recover (FIG. 2B (step II); FIG. 3D). As nutrients diffuse away from the nutrient disk, they promote the growth of tolerant bacteria that can form detectable colonies in the inhibition zone (FIG. 3C and FIG. 3D), whereas susceptible bacteria are not recovered by the addition of nutrients (FIG. 3A and FIG. 3B). Thus, whereas the standard assay shows a similar inhibition zone for a susceptible (FIG. 3A) and a tolerant strain (FIG. 3C), the TDtest discriminates between susceptible and tolerant strains by uncovering the surviving bacteria of the latter (FIG. 3B and FIG. 3D).

Example 3

The TDtest Detects Tolerant Bacteria

A. *E. coli* Strain W574

To test whether the late colonies appearing in the inhibition zone after the second step of the TDtest are growing simply because of the removal of the antibiotic disk, the TDtest was compared to various controls in W574. Specifically, TDtest on W574 with ertapenem showed the formation of bacterial colonies in the inhibition zone, indicating the high tolerance of this strain (FIG. 8D). In contrast, only few small colonies were obtained after incubation of W574 with the antibiotic, without the addition of a nutrient disk (FIG. 8C).

In view of the above, tolerant bacteria that have survived transient exposure to the antibiotic, such as according to the Kirby-Bauer disk diffusion assay, would not be detected because of the lack of nutrients supporting their visible growth.

B. *E. cloacae* Clinical Strain B340

The superiority of the TDtest in detecting tolerant bacteria strains over the standard the Kirby-Bauer disk diffusion was further demonstrated for the *E. cloacae* clinical strain B340. The bacteria were seeded on two agar dishes and an ampicillin disk was placed in the center of each dish (t=0). After 18 hours of incubation, the ampicillin disk in one plate was replaced with a glucose disk (FIG. 5B). 36 hours from the beginning of the experiment, B340 colonies were observed in the plate glucose was added, while a clear inhibition zone was maintained in the plate treated with ampicillin alone (FIG. 5A). Accordingly, the TDtest indicates that B340 is tolerant to ampicillin, while the standard diffusion assay fails to provide this information.

Example 4

The TDtest Detects Different Levels of Tolerance and Persistence

A qualitative evaluation of tolerance is made by the count of the number of colonies developed inside the growth inhibition zone after step II of the TDtest. "Low tolerance" is 0-10 colonies in the inhibition zone, "medium tolerance" is 10 to a few hundred colonies in the inhibition zone, and "high tolerance" is a bacterial lawn in the inhibition zone. Accordingly, the bacterial strain wt K-12 has low tolerance (FIG. 6A), the vapB mutant strain tbl3b has medium tolerance (FIG. 6B), and the metG mutant strain tbl5a, has high tolerance (FIG. 6C).

Furthermore, the TDtest can also detect sub-populations of tolerant bacteria, namely persistent bacteria. For example, strains bearing the hipA7 mutations have high persistence due to hyperactivation of the stringent response that results in the transient growth arrest of a sub-population of bacteria. The TDtest detects high tolerance in the hipA7 mutant (FIG. 6D-FIG. 6E).

Example 5

Colonies Detected with the TDtest are not Due to Resistant Mutants

Next, the inventors examined whether the bacterial colonies obtained in the inhibition zone by the use of the TDtest were not tolerant bacteria but rather resistant mutants. To that end, a TDtest, including both step I with imipenem and step II (glucose-containing disk) was performed on the bacterial strain W574 (FIG. 7A and FIG. 7B, respectively). A colony that grew inside the inhibition zone at the end of the experiment (FIG. 7B, white arrow) was picked and exposed to the disk diffusion assay with the same antibiotic. The lack of bacterial colonies in the inhibition zone as clearly seen in FIG. 7C, indicates that the colonies detected by the TDtest did not evolve from bacterial resistant mutations. Accordingly, the tolerant colonies that appear following the addition of the nutrient disk are not resistant.

Similar results were obtained with a different bacterial strain, tbl3a, when tested with imipenem (FIG. 14A-14I) and ampicillin (FIG. 15A-15I).

Example 6

TDtest Reveals Different Tolerance Levels in Clinical Isolates

Using the TDtest with ertapenem, the inventors were able to discriminate by tolerance level two ertapenem susceptible strains of *E. coli* (MIC<0.05 µg/ml). The absence of colonies inside the inhibition zone of strain U453 (FIG. 8A-8B) indicates that this strain has low tolerance. In contrast, the high number of W574 microcolonies growing inside the inhibition zone indicates that this strain has a high tolerance level (FIG. 8C-8D).

Measurement of the fraction of survival of a liquid culture under ertapenem at a concentration of 10 microgram/ml (similar to the mean serum concentration at 12 hours after 1 gram dosing), corroborate the TDtest results, namely the higher tolerance under ertapenem of W574 versus U453 (FIG. 8E).

Figures 9A, 9B, 9C:
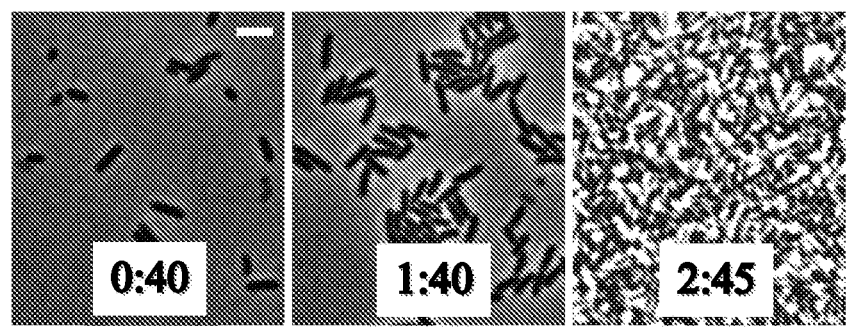
Figures 9D, 9E, 9F:
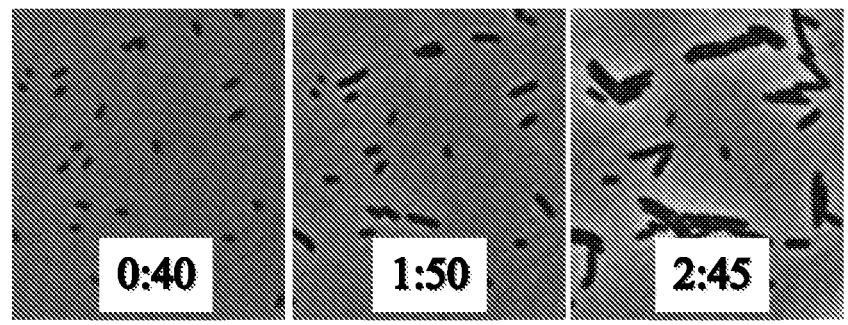

Moreover, direct monitoring by time-lapse microscopy showed that the difference in tolerance levels measured with the TDtest correlates with the cell-to-cell variability in the initiation of growth of the two strains in the absence of antibiotics. Whereas the low tolerance strain, U453, grows very uniformly and rapidly (FIG. 9A-FIG. 9C), cells of the medium tolerance strain, W574, vary in the time of initiation of growth (FIG. 9D-FIG. 9F). Accordingly, the tolerance is due to an extended lag phase of the more tolerant strain, W574. At t=40 min, the short lag strain (W453) has already started to grow. As beta-lactams target effectively only growing bacteria, the bacteria that initiated growth late would have a higher probability of surviving the ertapenem treatment.

Example 7

TDtest Enables the Rapid Detection of Antibiotics that are Effective Against Tolerant Bacteria Using the TDtest, the inventors were able to rapidly screen for antibiotics more effective against tolerant bacteria. The effects of two different antibiotics on the *E. coli* tolerant strain tbl3a, obtained by evolution under intermittent exposure to ampicillin, are shown in FIG. 10A-D. The bacteria were very tolerant to ampicillin (10 microgram) (FIG. 10A-FIG. 10B), but showed no tolerance to kanamycin (15 microgram) (FIG. 10C-FIG. 10D).

These findings were verified by measuring the survival of tbl3a in liquid culture after exposure to the two antibiotics. An overnight culture was diluted and exposed either to ampicillin (100 microgram/ml) or kanamycin (100 microgram/ml). In accordance to the results of the TDtests, the survival fraction under ampicillin was three orders of magnitude lower than under kanamycin (FIG. 10E). The large fraction of survivals in Ampicillin (12% after 2.6 hours) was predicted by the late colonies appearance, and is absent in Kanamycin (1.4E-8% after 2.6 hours).

Thus, although the standard "disk-diffusion" test did not point to an advantage of kanamycin over ampicillin against this strain, the TDtest revealed the potentially higher effectiveness of kanamycin against the tolerant bacteria.

Example 8

Two Alternative TDtest Detect Tolerant Bacteria

Tolerant bacteria are identified by the use of two different TDtest methods, the two-disks TDtest and the single disk TDtest. In this experiment, two plates were inoculated with a bacterium tolerant to ampicillin (tbl3a). Then, a disk comprising ampicillin was placed on the first plate (FIG. 11A), and a "two phase diffusion" disk containing both the antibiotic ampicillin and the nutrient glucose was applied to the second plate (FIG. 11B). The "two phase diffusion" disk is designed to allow the antibiotic to diffuse faster than the nutrient. After 18 hours, the ampicillin disk was removed from the first plate and replaced by a disk comprising glucose. The growth of the bacterium was monitored at several time points (0, 8, 17, 30 and 36 hours from the beginning of the test). In both plates, the bacterial colonies are well seen after 36 hours, indicating the efficiency of both methods in detecting tolerant bacteria.

The invention claimed is:

1. A tolerance diffusion kit for measuring tolerance or persistence of a microorganism to one or more antimicrobial agents, comprising:
    a) several disks containing one or more antimicrobial agents or one antimicrobial agent at different concentrations;
    b) at least one growth promoting agent provided on a growth promoting disk or as a solution in a vial;
    c) instructions for use of the tolerance diffusion kit;
    d) one or more microorganism growth plates; and
    e) means for detecting (i) at least one inhibition zone around said disks containing one or more antimicrobial agents or one antimicrobial agent at different concentrations, and (ii) the appearance of any microorganism colony within each detected inhibition zone.

* * * * *